United States Patent
Borchert et al.

(10) Patent No.: US 6,958,404 B2
(45) Date of Patent: Oct. 25, 2005

(54) METHOD FOR THE HYDROGENATION OF MALEIC ANHYDRIDE AND RELATED COMPOUNDS IN A FLUID BED REACTOR

(75) Inventors: Holger Borchert, Offstein (DE); Stephan Schlitter, Limburgerhof (DE); Michael Hesse, Worms (DE); Frank Stein, Bad Dürkheim (DE); Rolf-Hartmuth Fischer, Heidelberg (DE); Ralf-Thomas Rahn, Mannheim (DE); Alexander Weck, Freinsheim (DE); Markus Rösch, Oppenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 160 days.

(21) Appl. No.: 10/450,114

(22) PCT Filed: Dec. 7, 2001

(86) PCT No.: PCT/EP01/14395

§ 371 (c)(1),
(2), (4) Date: Jun. 11, 2003

(87) PCT Pub. No.: WO02/48130

PCT Pub. Date: Jun. 20, 2002

(65) Prior Publication Data

US 2004/0044230 A1 Mar. 4, 2004

(30) Foreign Application Priority Data

Dec. 11, 2000 (DE) ......................... 100 61 558

(51) Int. Cl.$^7$ .................. C07D 307/58; C07D 307/08; C07D 307/60
(52) U.S. Cl. ...................... 549/325; 549/233; 549/326; 549/508
(58) Field of Search ................................. 549/233, 325, 549/326, 508

(56) References Cited

U.S. PATENT DOCUMENTS

| | | | |
|---|---|---|---|
| 3,065,243 A | 11/1962 | Dunlop et al. | 260/343 |
| 3,580,930 A | 5/1971 | Miya et al. | 260/343 |
| 4,001,282 A * | 1/1977 | Miller | 549/325 |
| 4,006,165 A | 2/1977 | Michalczyk et al. | 260/343 |
| 4,083,809 A | 4/1978 | De Thomas et al. | 252/457 |
| 4,301,077 A | 11/1981 | Pesa et al. | 260/346 |
| 5,041,564 A * | 8/1991 | Buchanan, Jr. | 549/325 |
| 5,072,009 A | 12/1991 | Budge et al. | 549/508 |
| 5,122,495 A | 6/1992 | Taylor et al. | 502/183 |
| 5,142,067 A * | 8/1992 | Wegman et al. | 549/326 |
| 5,149,836 A | 9/1992 | De Thomas et al. | 549/325 |
| 5,326,889 A | 7/1994 | Suzuki et al. | 549/508 |
| 5,536,845 A | 7/1996 | Berthe et al. | 549/79 |
| 6,008,375 A | 12/1999 | Bergfeld et al. | 548/554 |

FOREIGN PATENT DOCUMENTS

| | | |
|---|---|---|
| EP | 322140 | 6/1989 |
| EP | 404408 | 12/1990 |
| EP | 638565 | 2/1995 |
| JP | 2233631 | 9/1990 |
| WO | 91/16132 | 10/1991 |
| WO | 95/22539 | 8/1995 |
| WO | 97/24346 | 7/1997 |
| WO | 99/35139 | 7/1999 |
| WO | 99/38856 | 8/1999 |

* cited by examiner

*Primary Examiner*—Bernard Dentz
(74) *Attorney, Agent, or Firm*—Novak Druce & Quigg

(57) ABSTRACT

$C_4$-dicarboxylic acids or derivatives thereof are hydrogenated in the gas phase in a fluidized-bed reactor. It is possible to use catalyst compositions known per se.

15 Claims, No Drawings

METHOD FOR THE HYDROGENATION OF MALEIC ANHYDRIDE AND RELATED COMPOUNDS IN A FLUID BED REACTOR

The present invention relates to a process for preparing unsubstituted or alkyl-substituted γ-butyrolocatone and tetrahydrofuran by catalytic hydrogenation in the gas phase of substrates selected from the group consisting of maleic acid and succinic acid and derivatives of these acids. For the purposes of the present invention, these are esters and anhydrides which, like the acids, can bear one or more alkyl substituents. The reaction is carried out in a fluidized-bed reactor.

The preparation of γ-butyrolactone (GBL) and tetrahydrofuran (THF) by gas-phase hydrogenation of maleic anhydride (MA) is a reaction which has been known for many years. Numerous catalyst systems for carrying out this catalytic reaction are described in the literature. Depending on the composition of the catalyst and the reaction parameters chosen, different product distributions are obtained using such catalysts.

Apart from MA, possible further starting materials for preparing GBL and THF are maleic acid itself, succinic acid and its anhydride and also the esters of these acids. If GBL and THF bearing alkyl substituents are to be prepared, the alkyl-substituted species corresponding to the abovementioned acids, esters and anhydrides can be used.

The catalysts used in the hydrogenation frequently comprise chromium, particularly in older processes. This is reflected in the patent literature in which there are a large number of patents and patent applications which disclose chromium-containing catalysts for the above-described hydrogenation reaction, with the hydrogenation in most cases being restricted to MA as starting material. U.S. Pat. No. 3,065,243 discloses a process in which copper chromite is employed as catalyst. According to the description and examples, this reaction results in formation of considerable amounts of succinic anhydride (SA) which has to be circulated. As is known, process engineering problems due to crystallization of SA or succinic acid formed therefrom with subsequent blocking of pipes frequently occur.

Further copper chromite catalysts for the hydrogenation of MA are disclosed, for example, in U.S. Pat. No. 3,580,930, U.S. Pat. No. 4,006,165, EP-A 638 565 and WO 99/38856.

The catalysts used in U.S. Pat. No. 5,072,009 have the formula $Cu_1Zn_bAl_cM_dO_x$ in which M is at least one element selected from the group consisting of the elements of groups IIA and IIIA, VA, VIII, Ag, Au, the elements of groups IIIB to VIIB and the lanthanides and actinides of the Periodic Table of the Elements, b is from 0.001 to 500, c is from 0.001 to 500 and d is from 0 to <200 and x corresponds to the number of oxygen atoms necessary according to valence criteria.

EP-A 0 404 408 discloses a catalyst whose catalytically active material corresponds essentially to the material disclosed in the above-cited U.S. Pat. No. 5,072,009 for hydrogenation of MA. The catalytically active material is used in immobilized form on a support as coated catalyst and not as all-active catalyst.

A two-stage catalyst system for the hydrogenation of MA is described in U.S. Pat. No. 5,149,836. The catalyst for the first stage is chromium-free while the catalyst for the second stage is based on Cu—Zn—Cr oxides.

Owing to the acute toxicity of chromium, more modern technologies are increasingly moving away from the use of chromium-containing catalysts. Examples of chromium-free catalyst systems may be found in WO 99/35139 (Cu—Zn oxide), WO 95/22539 (Cu—Zn—Zr) and U.S. Pat. No. 5,122,495 (Cu—Zn—Al oxide).

A catalyst made up exclusively of copper oxide and aluminum oxide for the gas-phase hydrogenation of MA to form GBL is disclosed in WO 97/24346. The use of a similar catalyst having in principle the same composition as in this patent application is disclosed in JP 2 233 631. The aim of that invention is to carry out the hydrogenation of MA in such a way that THF and 1,4-butanediol are formed as main products and only small amounts, if any, of GBL are formed. This is then achieved by the use of catalysts based on mixed Cu—Al oxides and by adherence to particular reaction conditions.

A frequent problem occurring in the above-described reactions is early deactivation of the catalyst. This can be due to various causes, for example chemical changes in the catalyst. To counter the problem of early deactivation of the catalyst, WO 91/16132 proposes a chromium-free catalyst which comprises CuO, ZnO, $Al_2O_3$ and optionally a processing aid and is reduced by means of hydrogen and then activated at >400° C. before use in the hydrogenation of MA. These catalysts are said to have a long life and not require the customary regeneration at short intervals.

It is also prior art in the hydrogenation to pass the gaseous MA or the derivative thereof in the presence of hydrogen through the reactor in which the catalyst is located as a fixed bed. This is also described in all the above-cited publications. In general, the hydrogenation reaction is carried out in such a way that contact of the catalyst with liquid MA or starting material is avoided. Liquid starting material coats the hot catalyst surface and then vaporizes from this, resulting in local areas of high MA concentration. In these places high molecular weight substances going as far as tar are formed and deposit on the catalyst, thus reducing its activity and selectivity. This is a further cause of the deactivation of the catalysts utilized in the hydrogenation of MA.

Low hydrogen/starting material ratios or high starting material concentrations are desirable in order to minimize the amount of hydrogen circulated and to aid the condensation of the products obtained, namely GBL and/or THF in the oxidation of MA. This reduces the proportion of product circulating in the hydrogenation circuit, thus significantly reducing subsequent reactions.

It is an object of the present invention to provide a process for the hydrogenation of maleic acid and/or succinic acid and/or the abovementioned derivatives, by means of which very low hydrogen/starting material ratios can be set without premature deactivation and reduction in the selectivity of the catalyst used due to decomposition products occurring.

We have found that this object is achieved by a process for the hydrogenation in the gas phase of $C_4$-dicarboxylic acids and/or their derivatives, wherein the reaction is carried out in a fluidized-bed reactor.

In a preferred embodiment of the present invention, the starting material is fed in liquid form into the fluidized bed.

For the purposes of the present invention, the term $C_4$-dicarboxylic acids and/or derivatives thereof refers to maleic acid and succinic acid which may be unsubstituted or bear one or more $C_1$–$C_6$-alkyl substituents and also the anhydrides and esters of these unsubstituted or alkyl-substituted acids. An example of such an acid is citraconic acid.

It has been found that carrying out the reaction in a fluidized-bed reactor, i.e. use of the catalyst in a fluidized bed, makes it possible to use high concentrations of the substrate to be hydrogenated without early deactivation of the catalyst being observed. Furthermore, high selectivities are achieved even at high concentration of the substrate to be hydrogenated. When reference is made in the present text to the hydrogen/starting material ratio, this is always based on the case in which only hydrogen without addition of an inert gas is mixed with the starting material. The terms in "concentration" and "WHSV" are always based on the total amount of reaction gas fed in, which may further comprise one or more inert gases.

As active composition for the catalysts used in the process of the present invention, it is in principle possible to employ all catalyst compositions known for the hydrogenation of MA or related compounds. Prerequisites for suitability in the process of the invention are the necessary or desired selectivity and activity and also sufficient mechanical abrasion resistance. Preferred catalysts are ones based on copper oxide which further comprise at least one additional metal selected from the group consisting of Al, Si, Zn, La, Ce, the elements of groups IIIA to VIIIA and groups IA and IIA and compounds thereof, preferably oxides.

For the purposes of the present invention, the group of the Periodic Table of the Elements is designated according to the old IUPAC nomenclature.

It is more preferred for the catalyst to comprise copper oxide and also a further metal selected from the group consisting of Al, Si, Ti, Zn, Zr, La, Ce and compounds thereof, preferably oxides. In particular, the catalyst is a combination of copper oxide with $Al_2O_3$, ZnO and/or $SiO_2$. The amount of Cu or its compounds, in particular the oxide, is $\geq 10\%$ by weight, preferably $\geq 25\%$ by weight. All other abovementioned components are present in amounts of $\leq 90\%$ by weight, preferably $\leq 75\%$ by weight.

The catalysts comprising the abovementioned materials are converted in a manner known per se into a shape suitable for use as a fluidized bed. These shapes are known to those skilled in the art, and preference is given to using powders. It is more preferred for the catalyst powder to be used in the form of fine particles having a mean particle diameter of from 10 to 1000 $\mu$m, in particular from 50 to 500 $\mu$m.

The catalysts are produced by methods known to those skilled in the art. Preference is given to processes in which the copper oxide is obtained in finely divided form intimately mixed with the other constituents. This is preferably achieved by precipitation reactions. Here, copper compounds dissolved in a solvent are precipitated by means of a precipitant in the presence of further metal compounds dissolved or suspended in the solvent, filtered off, washed, dried and, if desired, calcined. For example, the corresponding metal carbonates and/or hydroxides can be precipitated in aqueous solution, filtered off, washed, dried and, if desired, calcined. The metal carbonates or hydroxides are obtainable, for example, by dissolving the corresponding metal salts in water and adding sodium carbonate solution. Metal salts used are, for example, nitrates, sulfates, chlorides, acetates and/or oxalates. To achieve the particle size desired for use in a fluidized bed, the calcined catalyst is comminuted and sieved. However, it is also possible to sieve the dried catalyst precursor and to calcine it subsequently. A further possible way of producing the catalyst is to coat a pulverulent support with copper oxide and, if desired, other constituents. Suitable support materials are those known to a person skilled in the art, for example silicon oxide, aluminum oxide, silicon carbide or titanium dioxide having a mean particle diameter of from 10 to 1000 $\mu$m. Coating of the support material with copper oxide and, if desired, other components can be carried out by impregnation of the support with a solution of the metal salts in, for example, water. The support is subsequently dried and calcined to convert the metal salts into the oxides. Metal salts used are, for example, nitrates, sulfates, chlorides, acetates and/or oxalates.

To carry out the reaction, the starting material, i.e. the appropriate $C_4$-dicarboxylic acid or the derivative thereof, preferably MA, is brought into contact with hydrogen in the catalyst bed present as a fluidized bed. The hydrogen can be introduced in pure form or in admixture with other gaseous components. These further components have, depending on the reaction conditions, a favorable effect on the selectivity, activity and/or long-term stability. Examples of further components are water vapor, hydrocarbons such as methane, ethane and n-butane, and carbon monoxide. However, preference is generally given to using pure hydrogen.

In a preferred embodiment of the present invention, the starting material to be hydrogenated is fed in liquid form into the fluidized bed. Depending on the starting material used, which may be solid or liquid, prior melting may be necessary; for example, MA is used as a melt. This way of carrying out the reaction gives a number of advantages. For example, it is possible to set high starting material concentrations. Furthermore, in contrast to the processes customarily employed in which the starting material is generally introduced in gaseous form mixed with hydrogen, no apparatus for vaporizing the starting material or for stripping the starting material, in particular MA, after its preparation is necessary.

The ratio of hydrogen to the $C_4$-dicarboxylic acid or derivative thereof used as starting material, preferably MA, can be set to values of from 10 to 200 when using the fluidized-bed catalyst employed according to the present invention. The ratio is preferably in the range from 20 to 100. The concentration of starting material can be set to values of from 0.5 to 10% by volume, preferably from 1 to 8% by volume. It has been found that even low hydrogen/starting material ratios of about 10 and inlet concentrations of starting material of 10% by volume, which are customarily not selected, can be utilized when a fluidized-bed catalyst is used. When carrying out the process, the catalyst in the form of a powder is fluidized by means of the hydrogen feed stream, which may be mixed with other components, and the liquid starting material, i.e. a suitable $C_4$-dicarboxylic acid or derivative thereof, is fed directly into the fluidized bed. This is preferably achieved using a two-fluid nozzle by means of which the starting material is atomized as a mist by means of a stream of hydrogen. Preference is given to using MA as starting material. The liquid starting material vaporizes immediately after being fed in, exploiting the heat of the hydrogenation reaction.

Due to the fact that the starting material is metered in in liquid form, the maximum possible starting material concentration at the inlet is not limited by the saturation limit of the vapor pressure, in contrast to a fixed-bed reactor.

Owing to the intensive mixing of the catalyst in the fluidized bed, the formation of deposits otherwise observed at high starting material concentrations at the inlet to the reactor does not occur. It is assumed that the fluidization results in the catalyst particles laden with liquid starting material at the inlet traveling to regions of high hydrogen concentration. Here, the deposits are then eliminated by hydrogenation. In this way, the hydrogenation can be carried out using hydrogen/starting material ratios of down to 10, i.e. starting material concentrations at the inlet of 10% by volume. If the inlet concentration of starting material is increased to >10% by volume or the hydrogen/starting material ratio is reduced to values significantly below 10, there is a risk of the catalyst being wetted with liquid throughout the entire region of the fluidized bed and there forming relatively high-boiling components. The process of the present invention can also be carried out at hydrogen/starting material ratios above the abovementioned value of 200; however, such high hydrogen concentrations are generally not used because of the high amounts of gas which have to be circulated and the costs associated therewith.

The hydrogenation process of the present invention is carried out at from 200 to 400° C., preferably from 200° C. to 300° C. The pressures are from 1 to 100 bar, preferably from 1 to 50 bar. In choosing the volume flow of reaction gas (weight hourly space velocity, WHSV), care has to be taken to ensure that appropriate fluidization of the catalyst powder is achieved and complete conversion of the starting material or materials used takes place. The WHSV is preferably set to from 0.01 to 1.0 kg of starting material/h $l_{cat}$, in particular from 0.05 to 0.5 kg of starting material/h $l_{cat}$.

After the hydrogenation reaction is complete, the product mixture is fractionated by methods known to those skilled in the art and the product obtained is worked up. Preference is given to circulating part of the unreacted hydrogen and using it again in the hydrogenation.

The invention is illustrated by the following examples:

achieve better distribution of the starting materials, 20 standard l/h of hydrogen were fed through the annular gap into the fluidized bed. The main hydrogen stream of from 80 to 160 standard l/h was fed in through the distribution plate.

COMPARATIVE EXAMPLE 1

For comparison, data on the hydrogenation of MA in a fixed-bed reactor using a catalyst of identical composition in a pellet form are shown in table 2.

As comparison of the selectivities at an inlet concentration of MA=1.2 or 1.4% by volume shows, higher selectivities are achieved in the fluidized-bed reactor.

Even at a reduced pressure of only 3 bar compared to 5 bar in the fixed-bed reactor, complete conversion of MA is achieved using the fluidized-bed reactor. The yield of THF at high inlet concentrations of MA in the fluidized-bed reactor can be increased by increasing the pressure, preferably to at least 5 bar. Such pressures favor the formation of THF.

TABLE 1

Hydrogenation of MA in a fluidized bed using a CuO/Al$_2$O$_3$ catalyst

| Example | H$_2$ · MA ratio | C°$_{MA}$ % by volume | T (° C.) | P (bar) | WHSV (kg$_{MA}$/hl$_{cat}$) | Con$_{MA}$ (%) | S$_{SA}$ (%) | S$_{GBL}$ (%) | S$_{THF}$ (%) | S$_{remainder}$ (%) |
|---|---|---|---|---|---|---|---|---|---|---|
| 1 | 70 | 1.4 | 250 | 3 | 0.09 | 100 | <0.1 | 15 | 83 | 2 |
| 2 | 39 | 2.5 | 250 | 3 | 0.16 | 98 | 39 | 55 | 6 | 0 |
| 3 | 24 | 4.0 | 250 | 3 | 0.26 | 98 | 71 | 24 | 4 | 1 |
| 4 | 19 | 5.0 | 260 | 3 | 0.32 | 97 | 65 | 29 | 4 | 2 |
| 5 | 19 | 4.0 | 280 | 3 | 0.32 | 100 | 13 | 77 | 7 | 3 |
| 6 | 99 | 1.0 | 260 | 5 | 0.09 | 100 | 0 | 1 | 94 | 5 |
| 7 | 26 | 3.7 | 260 | 5 | 0.22 | 100 | <1 | <1 | 94 | 6 |
| 8 | 23 | 4.1 | 270 | 5 | 0.24 | 100 | <1 | 14 | 81 | 5 |

TABLE 2

Comparative experiment using an identical catalyst in a fixed-bed reactor (3 × 3 mm pellets)

| Comp. example | H$_2$ · MA ratio | C°$_{MA}$ % by volume | T (° C.) | P (bar) | WHSV (kg$_{MA}$/hl$_{cat}$) | Con$_{MA}$ (%) | S$_{SA}$ (%) | S$_{GBL}$ (%) | S$_{THF}$ (%) | S$_{remainder}$ (%) |
|---|---|---|---|---|---|---|---|---|---|---|
| 1 | 82 | 1.2 | 270 | 5 | 0.13 | 100 | 0 | 1 | 89 | 10 |

C°$_{MA}$ = inlet concentration of MA
WHSV = weight hourly space velocity
Con = conversion
S = selectivity to the respective product

EXAMPLES 1 TO 8

Hydrogenation of Maleic Anhydride.

The hydrogenation was carried out in a glass fluidized-bed reactor heated by means of circulating oil. As catalyst, from 65 to 130 ml of a catalyst which consisted of 60% CuO and 40% Al$_2$O$_3$ and had been milled to a powder (sieve fraction from 0.1 to 0.2 mm) were introduced and reduced by means of an N$_2$/H$_2$ mixture at 180° C. under atmospheric pressure before commencement of the reaction. After reduction of the catalyst had been completed, the pressure was increased to 3 or 5 bar under pure hydrogen and the reaction temperature was set. Liquid MA was fed directly into the fluidized bed, about 20 mm above the inflow plate. To

EXAMPLES 9 AND 10

Hydrogenation of Maleic Anhydride or a Maleic Anhydride/Maleic Acid Mixture

A melt consisting of 10% by weight of maleic acid (MAc) and 90% by weight of MA was fed into the fluidized bed. The catalyst used was the catalyst employed in examples 1 to 8. For comparison, the hydrogenation was carried out under identical conditions using pure MA.

As can be seen from table 3, there are no noticeable differences between the hydrogenation of pure MA and MA/MAc mixtures.

TABLE 3

Hydrogenation of MA and MA/MAc mixtures in the fluidized bed (reaction conditions: T = 250° C., WHSV = 0.09 kg of starting material/hl, P = 5 bar

| Feed | $Con_{MAc/MA}$ [%] | $S_{SA}$ [%] | $S_{GBL}$ [%] | $S_{THF}$ [%] | $S_{remainder}$ [%] |
|---|---|---|---|---|---|
| Pure MA | 100 | 0 | 1 | 95 | 5 |
| 90% by weight of MA + 10% by weight of MAc | 100 | 0 | 1 | 95 | 5 |

$C°_{MA}$ = inlet concentration of MA
WHSV = weight hourly space velocity
Con = conversion
S = selectivity to the respective product

We claim:

1. A process for the catalytic hydrogenation in the gas phase of $C_4$-dicarboxylic acids and/or their derivatives, wherein the reaction is carried out in a fluidized-bed reactor, and the $C_4$-dicarboxylic acid and/or the derivative thereof is fed in liquid form into the reactor.

2. A process as claimed in claim 1, wherein the catalyst is a catalyst which is based on copper oxide and further comprises at least one additional metal selected from the group consisting of Al, Si, Zn, Ce, La, the elements of groups IIIA to VIIIA and groups IA and IIA and compounds thereof, preferably oxides, where the further metal is preferably selected from the group consisting of Al, Si, Ti, Zn, Zr, La, Ce and compounds thereof, preferably oxides.

3. A process as claimed in claim 2, wherein the further metal is selected from the group consisting of Al, Si, Ti, Zn, Zr, La, Ce and compounds thereof.

4. A process as claimed in claim 2, wherein the compound is an oxide.

5. A process as claimed in claim 2, wherein the catalyst is a mixture of copper oxide with $Al_2O_3$, ZnO and/or $SiO_2$.

6. A process as claimed in claim 2, wherein the Cu or its compound is present in an amount of from $\geq 10\%$ by weight, and the remaining components are present in an amount of from $\leq 90\%$ by weight.

7. A process as claimed in claim 1, wherein the catalyst is used in the form of a powder.

8. A process as claimed in claim 7, wherein the powder has a particle diameter of from 10 to 1000 µm.

9. A process as claimed in claim 1, wherein the hydrogen used for the hydrogenation is employed in pure form or as a mixture with other components.

10. A process as claimed in claim 9, wherein the other compounds is selected from water vapor, methane, ethane, n-butane and/or carbon monoxide.

11. A process as claimed in claim 1, wherein the ratio of hydrogen to the $C_4$-dicarboxylic acid or derivative thereof used as starting material is from 10 to 200.

12. A process as claimed in claim 1, wherein the starting material concentration is from 0.5 to 10% by volume.

13. A process as claimed in claim 1, carried out at from 200 to 400° C. and pressures of from 1 to 100 bar.

14. A process as claimed in claim 1, wherein maleic anhydride and/or maleic acid are/is used as starting material.

15. A process as claimed in claim 1, wherein the $C_4$-dicarboxylic acid and/or derivative thereof is fed in liquid form into the fluidized bed.

* * * * *